(12) United States Patent
Ci (10) Patent No.: US 10,485,834 B2
(45) Date of Patent: Nov. 26, 2019

(54) CHINESE HERBAL ORAL PASTE FOR CONDITIONING PHLEGM-DAMPNESS CONSTITUTION AND PROCESSING METHOD THEREOF

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/967,075

(22) Filed: Apr. 30, 2018

(65) Prior Publication Data

US 2019/0192598 A1    Jun. 27, 2019

(30) Foreign Application Priority Data

Dec. 26, 2017    (CN) .......................... 2017 1 1428989

(51) Int. Cl.

| | | |
|---|---|---|
| *A61K 36/00* | (2006.01) | |
| *A61K 36/344* | (2006.01) | |
| *A61K 36/9066* | (2006.01) | |
| *A61K 36/8998* | (2006.01) | |
| *A61K 36/8994* | (2006.01) | |
| *A61K 36/9064* | (2006.01) | |
| *A61K 36/736* | (2006.01) | |
| *A61K 36/481* | (2006.01) | |
| *A61K 36/752* | (2006.01) | |
| *A61K 36/076* | (2006.01) | |
| *A61K 35/586* | (2015.01) | |
| *A61K 35/38* | (2015.01) | |
| *A61K 47/26* | (2006.01) | |
| *A61K 45/06* | (2006.01) | |
| *A61K 9/00* | (2006.01) | |
| *A61K 36/284* | (2006.01) | |
| *A61K 9/06* | (2006.01) | |

(52) U.S. Cl.
CPC .......... *A61K 36/344* (2013.01); *A61K 9/0053* (2013.01); *A61K 9/0056* (2013.01); *A61K 9/06* (2013.01); *A61K 35/38* (2013.01); *A61K 35/586* (2013.01); *A61K 36/076* (2013.01); *A61K 36/284* (2013.01); *A61K 36/481* (2013.01); *A61K 36/736* (2013.01); *A61K 36/752* (2013.01); *A61K 36/8994* (2013.01); *A61K 36/8998* (2013.01); *A61K 36/9064* (2013.01); *A61K 36/9066* (2013.01); *A61K 45/06* (2013.01); *A61K 47/26* (2013.01); *A61K 2236/13* (2013.01); *A61K 2236/51* (2013.01)

(58) Field of Classification Search
None
See application file for complete search history.

*Primary Examiner* — Qiuwen Mi
(74) *Attorney, Agent, or Firm* — Novick, Kim & Lee, PLLC; Allen Xue (57) ABSTRACT

A Chinese herbal oral paste includes the following raw material components: dangshen (*Codonopsis pilosula*), prepared white atractylodes rhizome, prepared black atractylodes rhizome, turmeric, unprocessed germinated barley, villous amomum fruit, coix seed, *Alisma plantago-aquatica* Linn., peach seed, tall gastrodia tuber, fuling, dried tangerine peel, seaweed, bitter apricot seed, cardamon fruit, perilla fruit, oriental waterplantain rhizome, ricepaperplant pith, Chinese waxgourd peel, kudzu vine root, unprocessed hawthorn fruit, milkvetch root, rice beans, lotus leaf, fortune eupatorium herb leaf, unprocessed cattail pollen, unprocessed rhubarb root and rhizome, inner membrane of chicken gizzard, white mustard seed, agastache rugosa, radish seed, xylitol, donkey-hide gelatin, and tortoise-plastron gelatin.

20 Claims, 1 Drawing Sheet

CHINESE HERBAL ORAL PASTE FOR CONDITIONING PHLEGM-DAMPNESS CONSTITUTION AND PROCESSING METHOD THEREOF

TECHNICAL FIELD

The present disclosure relates to the field of health foods, and particularly to a Chinese herbal oral paste for conditioning phlegm-dampness constitution and a processing method thereof.

BACKGROUND

In *Classification and Determination of Constitution in Traditional Chinese Medicine*, the China Association of Chinese Medicine classifies body constitutions of the human body into nine types, i.e., yin-yang harmony constitution, yang deficiency constitution, yin deficiency constitution, qi deficiency constitution, damp-heat constitution, phlegm-dampness constitution, qi depression constitution, blood stasis constitution, and allergic constitution, most of which are sub-healthy states.

The phlegm-dampness constitution manifests phlegm-dampness retention caused by phlegm formation due to dampness accumulation when the functions of internal organs (zang and fu) of the human body dysfunction, which easily leads to disordered transportation and transformation of qi (vital energy)-blood and body fluid, and water and dampness stagnation, accumulation of dampness and phlegm in phlegm wetness, usually showing obesity, fat abdomen, chest distress, excessive phlegm, drowsiness liability, heavy body and unpleasantness, addiction to greasy food and pure liquor, swelling tongue, and white greasy tongue fur, and is mostly caused by invasion of coldness and dampness, improper diet, inborn endowment, oldness and long illness, and lack of exercises, with different symptoms usually due to different parts of the phlegm-dampness retention. The tendency of morbidity is: consumptive thirst, stroke, chest obstruction and so on, with poor adaptability to plum rains and damp environments. An important treatment is eliminating dampness and phlegm, together with nursing and improving the phlegm-dampness constitution to prevent occurrence of the phlegm-dampness diseases.

Such sub-healthy constitution as phlegm-dampness constitution belongs to chronic diseases and has a relatively long disease course, and requires a long-term medication and gradual conditioning, in order to achieve the effects of eliminating dampness and phlegm. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. It is believed in the traditional Chinese medicine that since the human beings live in the natural world, physiological functions of the human body usually change with seasons, that is, "correspondence between man and nature". Winter is the season when the human body "stores energies", and appropriate nourishment can enhance the constitution, ward off diseases and strengthen the body, and prolong life, that is, conditioning in winter or nourishing in winter commonly mentioned in the traditional Chinese medicine. For the sub-healthy population with phlegm-dampness constitution, to choose a solid oral paste with a higher drug concentration and good taste, and being convenient to carry is more adapted to requirements of modern people.

SUMMARY

A main object of the present disclosure is to provide a Chinese herbal nourishing product suitable for conditioning in winter so as to condition phlegm-dampness constitution.

In order to achieve the above object, according to one aspect of the present disclosure, there is provided a Chinese herbal oral paste for conditioning phlegm-dampness constitution.

The Chinese herbal oral paste for conditioning phlegm-dampness constitution according to the present disclosure includes the following raw material components in parts by weight: 10-30 parts of dangshen (*Codonopsis pilosula*), 5-15 parts of prepared white atractylodes rhizome, 7-23 parts of prepared black atractylodes rhizome, 5-15 parts of turmeric, 8-22 parts of unprocessed germinated barley, 3-9 parts of villous amomum fruit, 5-15 parts of coix seed, 5-15 parts of *Alisma plantago-aquatica* Linn., 4-17 parts of peach seed, 5-17 parts of tall gastrodia tuber, 6-18 parts of fuling, 5-15 parts of dried tangerine peel, 12-23 parts of seaweed, 5-15 parts of bitter apricot seed, 1-5 parts of cardamon fruit, 4-16 parts of perilla fruit, 5-15 parts of oriental waterplantain rhizome, 3-9 parts of ricepaperplant pith, 10-30 parts of Chinese waxgourd peel, 10-30 parts of kudzu vine root, 12-28 parts of unprocessed hawthorn fruit, 5-15 parts of milkvetch root, 4-15 parts of rice beans, 10-30 parts of lotus leaf, 5-16 parts of fortune eupatorium herb leaf, 4-15 parts of unprocessed cattail pollen, 1-5 parts of unprocessed rhubarb root and rhizome, 4-9 parts of inner membrane of chicken gizzard, 7-17 parts of white mustard seed, 4-10 parts of agastache rugosa, 6-18 parts of radish seed, 20-40 parts of xylitol, 10-30 parts of donkey-hide gelatin, and 10-30 parts of tortoise-plastron gelatin.

Furthermore, the Chinese herbal oral paste for conditioning phlegm-dampness constitution according to the present disclosure includes the following raw material components in parts by weight: 15-25 parts of dangshen (*Codonopsis pilosula*), 7-13 parts of prepared white atractylodes rhizome, 10-20 parts of prepared black atractylodes rhizome, 7-13 parts of turmeric, 11-19 parts of unprocessed germinated barley, 4-8 parts of villous amomum fruit, 7-13 parts of coix seed, 7-13 parts of *Alisma plantago-aquatica* Linn., 7-13 parts of peach seed, 7-13 parts of tall gastrodia tuber, 9-15 parts of fuling, 7-13 parts of dried tangerine peel, 15-20 parts of seaweed, 7-13 parts of bitter apricot seed, 2-4 parts of cardamon fruit, 7-13 parts of perilla fruit, 7-13 parts of oriental waterplantain rhizome, 5-7 parts of ricepaperplant pith, 15-25 parts of Chinese waxgourd peel, 15-25 parts of kudzu vine root, 15-25 parts of unprocessed hawthorn fruit, 7-13 parts of milkvetch root, 7-13 parts of rice beans, 15-25 parts of lotus leaf, 7-13 parts of fortune eupatorium herb leaf, 7-13 parts of unprocessed cattail pollen, 1-3 parts of unprocessed rhubarb root and rhizome, 5-7 parts of inner membrane of chicken gizzard, 10-14 parts of white mustard seed, 6-8 parts of agastache rugosa, 9-15 parts of radish seed, 25-35 parts of xylitol, 15-25 parts of donkey-hide gelatin, and 15-25 parts of tortoise-plastron gelatin.

Furthermore, the Chinese herbal oral paste for conditioning phlegm-dampness constitution according to the present disclosure includes the following raw material components in parts by weight: 20 parts of dangshen (*Codonopsis pilosula*), 10 parts of prepared white atractylodes rhizome, 15 parts of prepared black atractylodes rhizome, 10 parts of turmeric, 15 parts of unprocessed germinated barley, 6 parts of villous amomum fruit, 10 parts of coix seed, 10 parts of *Alisma plantago-aquatica* Linn., 10 parts of peach seed, 10 parts of tall gastrodia tuber, 12 parts of fuling, 10 parts of dried tangerine peel, 20 parts of seaweed, 10 parts of bitter apricot seed, 3 parts of cardamon fruit, 10 parts of perilla fruit, 10 parts of oriental waterplantain rhizome, 6 parts of ricepaperplant pith, 20 parts of Chinese waxgourd peel, 20 parts of kudzu vine root, 20 parts of unprocessed hawthorn fruit, 10 parts of milkvetch root, 10 parts of rice beans, 20 parts of lotus leaf, 10 parts of fortune eupatorium herb leaf, 10 parts of unprocessed cattail pollen, 2 parts of unprocessed rhubarb root and rhizome, 6 parts of inner membrane of chicken gizzard, 12 parts of white mustard seed, 8 parts of agastache rugosa, 12 parts of radish seed, 30 parts of xylitol, 20 parts of donkey-hide gelatin, and 20 parts of tortoise-plastron gelatin.

In order to achieve the above object, according to the other aspect of the present disclosure, there is provided a processing method for a Chinese herbal oral paste for conditioning phlegm-dampness constitution.

The processing method for a Chinese herbal oral paste for conditioning phlegm-dampness constitution according to the present disclosure includes the following steps in sequence: preparation of materials, soaking, decoction, concentration, and collecting an oral paste.

Furthermore, the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by decoction concentration and stirring with gentle heat, until the drug liquid does not disperse when being dropped on paper, to obtain a vegetarian paste.

Furthermore, the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when dropped into clear water and does not disperse, and canning the resulted oral paste.

The melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

The Chinese herbal oral paste of the present disclosure has a higher drug concentration and good taste, is particularly suitable for health preserving in winter and conditioning the phlegm-dampness constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

The present disclosure provides a Chinese herbal oral paste for conditioning phlegm-dampness constitution, including the following raw material components: dangshen (*Codonopsis pilosula*), prepared white atractylodes rhizome, prepared black atractylodes rhizome, turmeric, unprocessed germinated barley, villous amomum fruit, coix seed, *Alisma plantago-aquatica* Linn., peach seed, tall gastrodia tuber, fuling, dried tangerine peel, seaweed, bitter apricot seed, cardamon fruit, perilla fruit, oriental waterplantain rhizome, ricepaperplant pith, Chinese waxgourd peel, kudzu vine root, unprocessed hawthorn fruit, milkvetch root, rice beans, lotus leaf, fortune eupatorium herb leaf, unprocessed cattail pollen, unprocessed rhubarb root and rhizome, inner membrane of chicken gizzard, white mustard seed, agastache rugosa, radish seed, xylitol, donkey-hide gelatin, and tortoise-plastron gelatin.

Tangshen is sweet in flavor and neutral in nature, acts on spleen and lung, nourishes the middle energizer and supplements qi, harmonizes stomach and promotes the secretion of body fluid, eliminates phlegm and relieves cough, and is used for reduced spleen-deficiency appetite and loose stool, numbness of limbs, palpitation, short of breath, mouth dryness, spontaneous perspiration, rectocele, and prolapse of the uterus.

Largehead atractylodes rhizome is bitter and sweet in flavor and warm in nature, acts on spleen and stomach, tonifies spleen and supplements qi, dries dampness and alleviates water retention, constrains sweating, prevents miscarriage, and is used for reduced spleen-deficiency appetite, abdominal distension diarrhea, phlegm and fluid retention and palpitation, edema, spontaneous perspiration, and fetal upset.

Prepared atractylodes rhizome is acrid and bitter in flavor and warm in nature, acts on spleen, stomach, and liver, dries dampness and tonifies spleen, dispels wind to eliminate cold, improves eyesight, and is used for dampness retention in middle jiao, abdominal fullness and distention, diarrhea, edema, beriberi paralysis, arthralgia due to wind-dampness, common cold due to wind-cold, nyctalopia, and faint and obscure eyesight.

Turmeric is acrid and bitter in flavor and warm in nature, acts on spleen and liver, activates blood stagnation, promotes circulation of qi, activates collaterals, relieves pain, and is used for chest and abdominal distention and fullness distending pain, arm pain, abdominal mass, blood stasis amenorrhea of women, postpartum stasis and retention abdominal pain, traumatic injury, and carbuncle.

Unprocessed germinated barley is sweet in flavor and neutral in nature, acts on spleen and stomach, promotes the circulation of qi and digestion, tonifies the spleen and stimulates appetite, terminates lactation and relieves flatulence, and is used for indigestion, abdominal distension, reduced spleen-deficiency appetite, milk stasis, breast tenderness, and delectation of women.

Villous amomum fruit is acrid in flavor and warm in nature, acts on spleen, stomach, and kidney, promotes the circulation of qi to regulate middle energizer, harmonizes stomach, refreshes spleen, and is used for abdominal pain and distension, anorexia and dyspepsia, dysphagia and vomiting, cold diarrhea and dysentery, and fetal movement.

Coix seed is sweet and light in flavor and cool in nature, acts on spleen, stomach, and lung, alleviates water retention and clears dampness, tonifies spleen and cures diarrhea, eliminates arthralgia syndromes, discharges pus, clears away toxic matters and removes stasis, and is used for edema, beriberi, difficult urination, spleen-deficiency diarrhea, dampness arthralgia muscular constriction, pulmonary abscess, intestinal carbuncle, excrescence, and cancerous protuberance.

Kelp is salty in flavor and cold in nature, acts on liver, stomach, and kidney, dissolves phlegm and softens hard masses, alleviates water retention and relieves swelling, and is used for thyroid tumor, scrofula, testicular swelling and pain, and phlegm-fluid retention edema.

Peach seed is bitter and sweet in flavor and neutral in nature, acts on heart, liver and large intestine, invigorates blood circulation to remove blood stasis, lubricates intestine to relax bowel, and relieves cough and asthma, and is used for amenorrhea and dysmenorrhea, lump in the abdomen, pulmonary abscess and intestinal carbuncle, traumatic injury, constipation due to intestinal dryness, and cough and dyspnea.

Tall gastrodia tuber is sweet in flavor and neutral in nature, acts on liver, calms endogenous wind, arrests convulsion, and is used for dizziness, head wind and headache, numbness of limbs, paralysis of half body, slurred speech, and infantile convulsion.

Fuling is sweet and light in flavor and neutral in nature, acts on heart, lung, spleen and kidney, alleviates water retention and clears dampness, tonifies spleen, calms the mind, and is used for edema and scanty urine, phlegm and fluid retention and dizziness and palpitation, reduced spleen-deficiency appetite, loose stool and diarrhea, uneasiness, and palpitation to insomnia.

Dried tangerine peel is bitter and acrid in flavor and warm in nature, acts on lung and spleen, regulates qi and tonifies spleen, dries dampness and resolves phlegm, and is used for abdominal fullness and distention, reduced appetite and vomiting, and cough with excessive phlegm.

Seaweed is bitter and salty in flavor and cold in nature, acts on liver, stomach, and kidney, dissolves phlegm, softens hard mass and resolves hard lump, alleviates water retention and relieves swelling, and is used for thyroid tumor, scrofula, testicular swelling and pain, and phlegm-fluid retention edema.

Bitter apricot seed is bitter in flavor and slightly warm in nature, acts on lung and large intestine, relieves cough and asthma, lubricates intestine to relax bowel, and is used for cough and dyspnea, and constipation due to intestinal dryness.

Cardamon fruit is acrid in flavor and warm in nature, acts on spleen and stomach, resolves dampness and promotes the circulation of qi, warms the middle energizer and arrests vomiting, stimulates appetite and promotes digestion, and is used for dampness obstruction and qi stagnation, incoordination between spleen and stomach, abdominal fullness and distention, poor appetite, beginning of damp-warm syndrome, oppression in the chest without hunger, stomach cold vomiting, and indigestion.

Perilla fruit is acrid in flavor and warm in nature, acts on lung and large intestine, descends qi and eliminates phlegm, relieves cough and asthma, lubricates intestine to relax bowel, and is used for reversed flow of qi due to phlegm obstruction, cough and dyspnea, and constipation due to intestinal dryness.

Oriental waterplantain rhizome is sweet in flavor and cold in nature, acts on kidney and bladder, alleviates water retention, promotes diuresis, reduces heat, and is used for difficult urination, edema distention, vomiting, diarrhea, phlegm-fluid retention, dermatophytosis, gonorrhea, and hematuria.

Ricepaperplant pith is sweet and light in flavor and slight cold in nature, acts on lung and stomach, clears away dampness and alleviates water retention, promotes lactation, and is used for stranguria, difficult urination, edema, jaundice, damp-warm diseases, scanty dark urine, postpartum hypogalactia, amenorrhea, leucorrhoea disease, dampness-warm dark urine, stranguria, edema and oliguria, and breast milk stoppage.

Chinese waxgourd peel is sweet in flavor and cool in nature, acts on spleen and small intestine, promotes urination and relieves swelling, and is used for edema distention, difficult urination, summer-heat thirst, and scanty dark urine.

Kudzu vine root is sweet and acrid in flavor and cool in nature, acts on lung and stomach, relieves the muscles and skin and allays fever, promotes eruption, promotes secretion of body fluid and quenches thirst, invigorates yang and cures diarrhea, and is used for treatment of syndrome of fever, sever back pain, measles without adequate eruption, thirst caused by fever, yin-deficiency consumptive thirst, heat diarrhea, and spleen-deficiency diarrhea.

Unprocessed hawthorn fruit is sour and sweet in flavor, and slightly warm in nature, acts on spleen, stomach, and liver, promotes digestion and tonifies stomach, promotes the circulation of qi to dissipate stasis, resolves turbidity and lowers lipid, and is used for meat-type food accumulation, abdominal fullness and distention, dysentery abdominal pain, blood stasis amenorrhea, puerperal blood stasis, prickling in heart and abdomen, chest stuffiness and pains, colic pain, and hyperlipemia.

Milkvetch root is sweet in flavor and slightly warm in nature, acts on lung, spleen, liver, and kidney, tonifies defensive-qi and secures the exterior, replenishes qi and invigorates yang, draws toxin and promotes tissue generation, alleviates water retention and relieves swelling, and is used for phlegm-dampness lassitude, reduced appetite and loose stool, sinking of qi of middle energizer, rectocele due to chronic diarrhea, spontaneous perspiration and night sweating, blood-deficiency etiolation, dorsal furuncle borderless swelling, phlegm-dampness edema, and internal-heat consumptive thirst.

Rice beans are sweet and sour in flavor and neutral in nature, act on heart and small intestine, alleviate water retention and relieve swelling, clear away toxic materials and discharge pus, and are used for edema distention, beriberi edema, jaundice and dark urine, wind-dampness pyretic arthralgia, carbuncle, and intestinal carbuncle and stomachache.

Lotus leaf is bitter in flavor and neutral in nature, acts on liver, spleen, and stomach, clears summer-heat and resolves dampness, sends up lucid yang, cools blood to stop bleeding, and is used for summer-heat polydipsia, summer-dampness diarrhea, spleen-deficiency diarrhea, and hematochezia, metrorrhagia and metrostaxis.

Fortune eupatorium herb leaf is acrid in flavor and neutral in nature, acts on spleen, stomach, and lung, clears summer-heat, repels foulness, resolves dampness, regulates menstruation, and is used for summer-heat and dampness, chill and fever headache, retention of dampness pathogen in the interior, fullness and distending pain in the chest and upper abdomen and anorexia, mouth dryness and greasy coating, and irregular menstruation.

Unprocessed cattail pollen is sweet in flavor and neutral in nature, acts on liver and pericardium meridian, stops bleeding, dissolves stasis, treats stranguria, and is used for hematemesis, bleeding from five sense organs or subcutaneous tissue, hemoptysis, metrorrhagia and metrostaxis, traumatic bleeding, amenorrhea and dysmenorrhea, prickling in chest and stomach, traumatic gall, and bloody stranguria.

Unprocessed rhubarb root and rhizome is bitter in flavor and cold in nature, acts on stomach, large intestine, liver, and spleen, treats indigestion, clears dampness-heat, discharges fire, cools blood, removes blood stasis, eliminates toxic matters, and is used for constipation due to sthenic fever accumulation, blood-heat haematemesis, bloodshot eye and swelling in throat, carbuncle and furuncles, intestinal carbuncle and abdominal pain, blood stasis amenorrhea, puerperal blood stasis, traumatic injury, dampness-heat dysentery, jaundice and dark urine, stranguria, edema, and external treatment of burn.

Inner membrane of chicken gizzard is sweet in flavor and neutral in nature, acts on spleen, stomach, small intestine, and bladder, tonifies stomach and promotes digestion, arrests seminal emission, treats stranguria and removes urinary calculus, and is used for indigestion, vomiting and diarrhea, infantile malnutrition, enuresis, gonobolia, urethral calculus pain, and gallbladder distention and hypochondriac pain.

White mustard seed is acrid in flavor and warm in nature, and non-toxic, acts on lung and stomach, warms lung, eliminates phlegm, and reinforces qi, removes stagnation in breast and removes obstruction in collateral to stop pain, and is used for cold-phlegm dyspnea with cough, distending pain in chest and hypochondrium, phlegm retention in main and collateral channels, joint numbness, pain, phlegm-dampness ulceration, and furuncle pyogenic infections.

Agastache rugosa is acrid in flavor and slightly warm in nature, acts on spleen, stomach, and lung, eliminates dampness with aromatics, regulates the middle energizer to stop vomiting, relieves exterior syndrome and relieves summer-heat, and is used for dampness turbidity blocking, fullness and distending pain in the chest and upper abdomen and anorexia and vomiting, exterior syndromes of summer-dampness, beginning of damp-warm syndrome, fever lassitude, oppression in the chest, cold and damp summer-heat closure, abdominal pain and diarrhea, nasosinusitis and headache.

Radish seed is acrid and sweet in flavor and neutral in nature, acts on the lung, spleen, and stomach, promotes digestion and eliminates flatulence, descends qi and eliminates phlegm, and is used for fullness with food stagnation, abdominal distension, constipation, indigestion diarrhea, phlegm obstruction cough and asthma.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea disease.

The phlegm-dampness constitution is featured by obesity, fat and soft abdomen, yellowish complexion and edema, excessive sticky sweating, thick and greasy tongue fur, drowsiness liability, heavy body and unpleasantness. The conditioning and treatment of the phlegm-dampness constitution should be based on the principle of drying dampness to eliminate phlegm, resolving dampness to nurse the body, and promoting the rising of clear yang qi, and enabling healthy transportation of the spleen and stomach so as to transport water and dampness. In the present application, by using these drugs in combination, san jiao (triple energizer) is thoroughly smoothed and regulated, qi and blood are transported, both the interior and the exterior are treated, excessive phlegm, water, dampness, and stagnation are eliminated, thus the phlegm-dampness constitution is improved, and further the object of losing weight is achieved. With the multiple types of drug materials of large dosages, efficacies of the various drug materials generate a synergistic effect, with the functions of drying dampness to eliminate phlegm, and the phlegm-dampness constitution can be conditioned, so that people are vigorous with strong resistibility, and the occurrence of diseases is avoided. With the conditioning for such constitution, it is more targeted and will not create side effects, without harm to the human body at all, and can achieve certain efficacy of strengthening the body.

Figure 1:
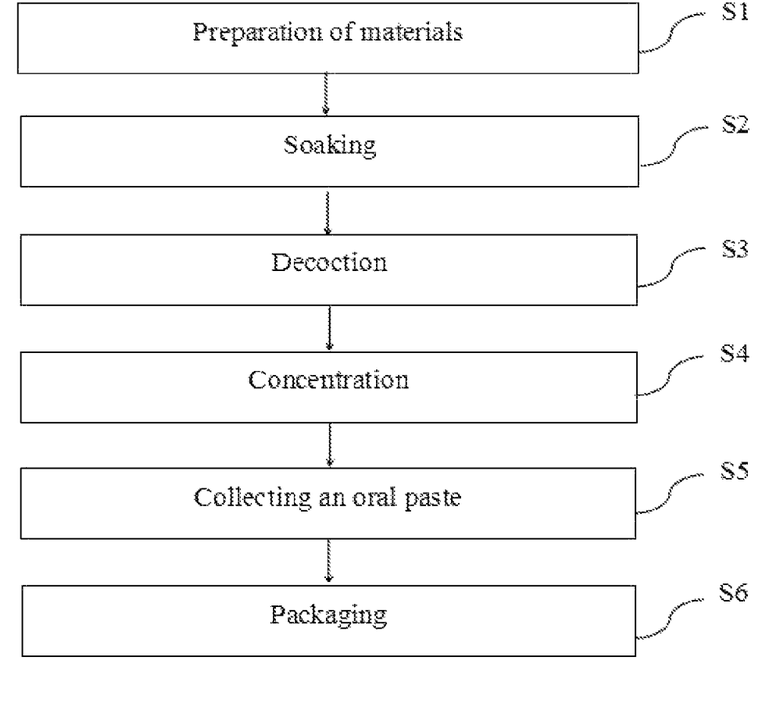
FIG. 1 is a flow chart of a processing technology for a Chinese herbal oral paste of one of embodiments of the present disclosure.

As shown in FIG. 1, the processing method for the Chinese herbal oral paste for conditioning phlegm-dampness constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1

A Chinese herbal oral paste for conditioning phlegm-dampness constitution includes the following raw material components in parts by weight: 10 parts of dangshen (*Codonopsis pilosula*), 5 parts of prepared white atractylodes rhizome, 7 parts of prepared black atractylodes rhizome, 5 parts of turmeric, 8 parts of unprocessed germinated barley, 3 parts of villous amomum fruit, 5 parts of coix seed, 5 parts of *Alisma plantago-aquatica* Linn., 4 parts of peach seed, 5 parts of tall gastrodia tuber, 6 parts of fuling, 5 parts of dried tangerine peel, 12 parts of seaweed, 5 parts of bitter apricot seed, 1 part of cardamon fruit, 4 parts of perilla fruit, 5 parts of oriental waterplantain rhizome, 3 parts of ricepaperplant pith, 10 parts of Chinese waxgourd peel, 10-30 parts of kudzu vine root, 12 parts of unprocessed hawthorn fruit, 5 parts of milkvetch root, 4 parts of rice beans, 10 parts of lotus leaf, 5 parts of fortune eupatorium herb leaf, 4 parts of unprocessed cattail pollen, 1 part of unprocessed rhubarb root and rhizome, 4 parts of inner membrane of chicken gizzard, 7 parts of white mustard seed, 4 parts of agastache rugosa, 6 parts of radish seed, 20 parts of xylitol, 10 parts of donkey-hide gelatin, and 10 parts of tortoise-plastron gelatin.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering the drug juice with gauze, then soaking filtered dregs of decoction with clear water and decocting the soaked dregs of decoction with low heat for 1 hour, repeated 4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 2

A Chinese herbal oral paste for conditioning phlegm-dampness constitution includes the following raw material components in parts by weight: 10-30 parts of dangshen (*Codonopsis pilosula*), 15 parts of prepared white atractylodes rhizome, 23 parts of prepared black atractylodes rhizome, 15 parts of turmeric, 22 parts of unprocessed germinated barley, 9 parts of villous amomum fruit, 15 parts of coix seed, 15 parts of *Alisma plantago-aquatica* Linn., 17 parts of peach seed, 17 parts of tall gastrodia tuber, 18 parts of fuling, 15 parts of dried tangerine peel, 23 parts of seaweed, 15 parts of bitter apricot seed, 5 parts of cardamon fruit, 16 parts of perilla fruit, 15 parts of oriental waterplantain rhizome, 9 parts of ricepaperplant pith, 30 parts of Chinese waxgourd peel, 30 parts of kudzu vine root, 28 parts of unprocessed hawthorn fruit, 15 parts of milkvetch root, 15 parts of rice beans, 30 parts of lotus leaf, 16 parts of fortune eupatorium herb leaf, 15 parts of unprocessed cattail pollen, 5 parts of unprocessed rhubarb root and rhizome, 9 parts of inner membrane of chicken gizzard, 17 parts of white mustard seed, 10 parts of agastache rugosa, 18 parts of radish seed, 40 parts of xylitol, 30 parts of donkey-hide gelatin, and 30 parts of tortoise-plastron gelatin.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering the drug juice with gauze, then soaking filtered dregs of decoction with clear water and decocting the soaked dregs of decoction with low heat for 1 hour, repeated 2 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 3

A Chinese herbal oral paste for conditioning phlegm-dampness constitution includes the following raw material components in parts by weight: 15 parts of dangshen (*Codonopsis pilosula*), 7 parts of prepared white atractylodes rhizome, 10 parts of prepared black atractylodes rhizome, 7 parts of turmeric, 11 parts of unprocessed germinated barley, 4 parts of villous amomum fruit, 7 parts of coix seed, 7 parts of *Alisma plantago-aquatica* Linn., 7 parts of peach seed, 7 parts of tall gastrodia tuber, 9 parts of fuling, 7 parts of dried tangerine peel, 15 parts of seaweed, 7 parts of bitter apricot seed, 2 parts of cardamon fruit, 7 parts of perilla fruit, 7 parts of oriental waterplantain rhizome, 5 parts of ricepaperplant pith, 15 parts of Chinese waxgourd peel, 15 parts of kudzu vine root, 15 parts of unprocessed hawthorn fruit, 7 parts of milkvetch root, 7 parts of rice beans, 15 parts of lotus leaf, 7 parts of fortune eupatorium herb leaf, 7 parts of unprocessed cattail pollen, 1 part of unprocessed rhubarb root and rhizome, 5 parts of inner membrane of chicken gizzard, 10 parts of white mustard seed, 6 parts of agastache rugosa, 9 parts of radish seed, 25 parts of xylitol, 15 parts of donkey-hide gelatin, and 15 parts of tortoise-plastron gelatin.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 10 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice;

combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 4

A Chinese herbal oral paste for conditioning phlegm-dampness constitution includes the following raw material components in parts by weight: 25 parts of dangshen (*Codonopsis pilosula*), 13 parts of prepared white atractylodes rhizome, 20 parts of prepared black atractylodes rhizome, 13 parts of turmeric, 19 parts of unprocessed germinated barley, 8 parts of villous amomum fruit, 13 parts of coix seed, 13 parts of *Alisma plantago-aquatica* Linn., 13 parts of peach seed, 13 parts of tall gastrodia tuber, 9-15 parts of fuling, 13 parts of dried tangerine peel, 20 parts of seaweed, 13 parts of bitter apricot seed, 2-4 parts of cardamon fruit, 13 parts of perilla fruit, 13 parts of oriental waterplantain rhizome, 7 parts of ricepaperplant pith, 25 parts of Chinese waxgourd peel, 25 parts of kudzu vine root, 25 parts of unprocessed hawthorn fruit, 13 parts of milkvetch root, 13 parts of rice beans, 25 parts of lotus leaf, 13 parts of fortune eupatorium herb leaf, 13 parts of unprocessed cattail pollen, 3 parts of unprocessed rhubarb root and rhizome, 7 parts of inner membrane of chicken gizzard, 14 parts of white mustard seed, 8 parts of agastache rugosa, 15 parts of radish seed, 35 parts of xylitol, 25 parts of donkey-hide gelatin, and 25 parts of tortoise-plastron gelatin.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 12 h, with the water over the raw materials by 18 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 5

A Chinese herbal oral paste for conditioning phlegm-dampness constitution includes the following raw material components in parts by weight: 20 parts of dangshen (*Codonopsis pilosula*), 10 parts of prepared white atractylodes rhizome, 15 parts of prepared black atractylodes rhizome, 10 parts of turmeric, 15 parts of unprocessed germinated barley, 6 parts of villous amomum fruit, 10 parts of coix seed, 10 parts of *Alisma plantago-aquatica* Linn., 10 parts of peach seed, 10 parts of tall gastrodia tuber, 12 parts of fuling, 10 parts of dried tangerine peel, 20 parts of seaweed, 10 parts of bitter apricot seed, 3 parts of cardamon fruit, 10 parts of perilla fruit, 10 parts of oriental waterplantain rhizome, 6 parts of ricepaperplant pith, 20 parts of Chinese waxgourd peel, 20 parts of kudzu vine root, 20 parts of unprocessed hawthorn fruit, 10 parts of milkvetch root, 10 parts of rice beans, 20 parts of lotus leaf, 10 parts of fortune eupatorium herb leaf, 10 parts of unprocessed cattail pollen, 2 parts of unprocessed rhubarb root and rhizome, 6 parts of inner membrane of chicken gizzard, 12 parts of white mustard seed, 8 parts of agastache rugosa, 12 parts of radish seed, 30 parts of xylitol, 20 parts of donkey-hide gelatin, and 20 parts of tortoise-plastron gelatin.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 9 h, with the water over the raw materials by 12 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice;

combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Experiment Example 1

Below is a test of effects of the Chinese herbal oral paste for conditioning phlegm-dampness constitution prepared according to Embodiment 5 of the present disclosure.

Basic conditions of cases: 120 clinical cases of phlegm-dampness constitution, including 60 male cases and 60 female cases, among which the youngest was 18 years old, and the oldest was 72 years old. 40 cases suffered from repeated attacks of cough, excessive sticky and greasy phlegm or heavy and lumped phlegm, white in color or grayish, worsened when taking sweet and greasy food, physical lassitude, with white greasy tongue fur and soft-smooth pulse; 40 cases suffered from abdomen blockage discomfort, worsened especially when taking food, chest distress, dizziness, heavy body and drowsiness, nausea and vomiting, poor appetite and digestion, tastelessness in the mouth and hydroadipsia, with regular or unsolid bowel movement, white greasy tongue fur, and soft-smooth pulse; 40 cases suffered from head heaviness and darkness, chest distress and nausea, vomiting and sputum, and reduced appetite and sleepiness, with white greasy tongue fur and soft-smooth pulse.

Usage and dosage: 25 g each time, once a day. Brew 25 g of the oral paste with boiling water in a cup, and stir the oral paste to make it melt for administration.

Evaluation criteria for therapeutic effects:

Cured: clinical symptoms completely disappeared, and normal life was restored.

Taking effect: most of the symptoms disappeared, with great improvements.

Effective: a small part of clinical symptoms disappeared, and various signs were gradually improved.

Ineffective: symptoms and signs were not obviously improved.

Result statistics: 48 cases cured, taking effect for 33 cases, effective to 32 cases, and ineffective to 7 cases, i.e., effective to 113 cases in total, therefore the total effective rate was 94.16%.

Experiment Example 2: Animal Experiment

In order to manifest that a composition prepared in the present disclosure has unpredictable technical effects to the phlegm-dampness symptoms, rats were fed with high-fat diet, and lived in humid environment (85%-90% of humidity, and 18-20° C. of temperature) for 12 weeks, to create phlegm-dampness models. The specific experiment is as follows:

1. Experiment Animals:

SD rats, half males and half females, with a body weight of 200±10 g.

2. Experiment Supplies

Chinese herbal oral paste prepared according to Embodiments 1-5 of the present application;

High-fat diet.

3. Experiment Process 3.1 Creating Models

The rats were randomly divided into a blank control group, a model group, and 5 experiment groups of Embodiments 1-5. The blank control group was fed routinely, and ate and drank freely, while the other groups were fed with the high-fat diet from the beginning of the experiment, and lived in a humid environment (85%-90% of humidity, and 18-20° C. of temperature) continuously for 12 weeks, then the rats were subjected to intraperitoneal injection of 0.2 mL/100 g of 3% pentobarbital sodium to anaesthetize, and blood was taken from the ventral abdominal artery.

3.2 Experiment Grouping

The rats were randomly divided into 7 groups: the blank control group, the model group, and 5 experiment groups, 20 rats in each group; the rats of the experiment groups were respectively orally administered with the Chinese herbal oral paste prepared according to Embodiments 1-5 of the present application, and the rats of the blank control group were orally administered with an equal amount of normal saline.

3.3 Statistical Manner

The statistics were made with the SPSS12.0 software, and one-way analysis of variance was used in the method. The analysis of variance was used for comparison among groups. The difference of $P<0.05$ indicates statistical significance.

4. Behavior Observation

Monitoring of general conditions: observing the situations of spirit, activity, etc. of the model animals, and scoring them according to the specific representation with reference to a scoring table of Table 1. Scoring results are shown in Table 2.

slightly white tail and nose lacking lustre, loose and stinky excrement, of which the score of biological representation was significantly increased compared with the blank control group ($P<0.01$); compared with the model group, the rats of the 5 experiment groups of the present application reacted slightly slowly, with reduced locomotor activities, slightly loose and soft skin, reddish tail and nose lacking lustre; dry and shaped-up excrement, of which the score of biological representation was significantly decreased ($P<0.01$).

5. Detection of Serum TC, TG, HDLC, LDLC, and VLDLC

Blood was taken from the ventral abdominal artery, and after standing for 4 h, underwent centrifugation at 6000 rpm, and then the serum was taken after 5 mins, and subjected to automatic biochemical detection for five indexes, namely, total cholesterol (TC), triglyceride (TG), high density lipoprotein cholesterol (HDLC), low density lipoprotein cholesterin (LDLC), and very low density lipoprotein cholesterol (VLDLC).

The experiment results show that compared with the blank control group, the rats of the model group had significantly increased contents of serum TC, HDLC, LDLC, and VLDLC and significantly decreased TG. Compared with the model group, the five experiment groups of

TABLE 1

Experimental Rats Biological Characterization Semi-quantitative Scoring Observation Table

| Score | Spirit Situation | Skin and Hair | Color of Ear and Tail | Excrement |
|---|---|---|---|---|
| 0 | Lively and active | Tight connection between skin and fat, flexible skin, and bright and silky hair | Ruddy and lustrous | Dry and shaped-up |
| 1 | Slightly slow in reacting, with reduction of locomotor activities | Slightly loose skin, with reduced tension, dry yellow hair without lustre | Reddish and lacking lustre | Gummy, soft, and tangible |
| 2 | Tired and lazy, sluggish | Loose skin, more fat, dry or tangled and wavy hair | Slightly white and lacking lustre | Unshaped, loose, and stinky |
| 3 | Inert, with decreased antagonistic behavior | Loose skin, obesity, yellow and sparse hair, with loss of hair | Pale or cyan | Loose, green-brown, gummy and soft, and fetid |

TABLE 2

Observation Table of Biological Representation of Rats of Various Experiment Groups

| Group | n | Score |
|---|---|---|
| Blank control group | 20 | 1.27 ± 0.62 |
| Model Group | 20 | 4.55 ± 0.75** |
| Embodiment 1 | 20 | 1.30 ± 0.43## |
| Embodiment 2 | 20 | 1.43 ± 0.49## |
| Embodiment 3 | 20 | 1.39 ± 0.66## |
| Embodiment 4 | 20 | 1.33 ± 0.70## |
| Embodiment 5 | 20 | 1.35 ± 0.54## |

Notes:
compared with the blank control group, **$P<0.01$, and compared with the model group, ##$P<0.01$ It can be seen from Table 2 that the experiment results of the scoring of the biological representation of the rats of various groups show that the rats of the blank control group were lively and active, and quick-witted; the rats of the model group seemed tired and lazy, weary in spirit, sluggish in action, obese in body, gradually took less food, with the present application have significantly decreased TC, HDLC, LDLC, and VLDLC and significantly increased TG.

The experiment results show that the Chinese herbal oral paste of Embodiments 1-5 of the present application have good conditioning and curing effects to the phlegm-dampness syndromes.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can serve an effect of sustained release, and a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning phlegm-dampness constitution, comprising the following raw material components in parts by weight: 10-30 parts of dangshen, 5-15 parts of prepared white atractylodes rhizome, 7-23 parts of prepared black atractylodes rhizome, 5-15 parts of turmeric, 8-22 parts of unprocessed germinated barley, 3-9 parts of villous amomum fruit, 5-15 parts of coix seed, 5-15 parts of kelp Linn., 4-17 parts of peach seed, 5-17 parts of tall gastrodia tuber, 6-18 parts of fuling, 5-15 parts of dried tangerine peel, 12-23 parts of seaweed, 5-15 parts of bitter apricot seed, 1-5 parts of cardamon fruit, 4-16 parts of perilla fruit, 5-15 parts of oriental waterplantain rhizome, 3-9 parts of ricepaperplant pith, 10-30 parts of Chinese waxgourd peel, 10-30 parts of kudzu vine root, 12-28 parts of unprocessed hawthorn fruit, 5-15 parts of milkvetch root, 4-15 parts of rice beans, 10-30 parts of lotus leaf, 5-16 parts of fortune eupatorium herb leaf, 4-15 parts of unprocessed cattail pollen, 1-5 parts of unprocessed rhubarb root and rhizome, 4-9 parts of inner membrane of chicken gizzard, 7-17 parts of white mustard seed, 4-10 parts of agastache rugosa, 6-18 parts of radish seed, 20-40 parts of xylitol, 10-30 parts of donkey-hide gelatin, and 10-30 parts of tortoise-plastron gelatin.

2. The Chinese herbal oral paste for conditioning phlegm-dampness constitution of claim 1, comprising the following raw material components in parts by weight: the dangshen is 15-25 parts by weight, the prepared white atractylodes rhizome is 7-13 parts by weight, the prepared black atractylodes rhizome is 10-20 parts by weight, the turmeric is 7-13 parts by weight, the unprocessed germinated barley is 11-19 parts by weight, the villous amomum fruit is 4-8 parts by weight, the coix seed is 7-13 parts by weight, the kelp is 7-13 parts by weight, the peach seed is 7-13 parts by weight, the tall gastrodia tuber is 7-13 parts by weight, the fuling is 9-15 parts by weight, the dried tangerine peel is 7-13 parts by weight, the seaweed is 15-20 parts by weight, the bitter apricot seed is 7-13 parts by weight, the cardamon fruit is 2-4 parts by weight, the perilla fruit is 7-13 parts by weight, the oriental waterplantain rhizome is 7-13 parts by weight, the ricepaperplant pith is 5-7 parts by weight, the Chinese waxgourd peel is 15-25 parts by weight, the kudzu vine root is 15-25 parts by weight, the unprocessed hawthorn fruit is 15-25 parts by weight, the milkvetch root is 7-13 parts by weight, the rice beans is 7-13 parts by weight, the lotus leaf is 15-25 parts by weight, the fortune eupatorium herb leaf is 7-13 parts by weight, the unprocessed cattail pollen is 7-13 parts by weight, the unprocessed rhubarb root and rhizome is 1-3 parts by weight, the inner membrane of chicken gizzard is 5-7 parts by weight, the white mustard seed is 10-14 parts by weight, the agastache rugosa is 6-8 parts by weight, the radish seed is 9-15 parts by weight, the xylitol is 25-35 parts by weight, the donkey-hide gelatin is 15-25 parts by weight, and the tortoise-plastron gelatin is 15-25 parts by weight.

3. The Chinese herbal oral paste for conditioning phlegm-dampness constitution of claim 1, comprising the following raw material components in parts by weight: the dangshen is 20 parts by weight, the prepared white atractylodes rhizome is 10 parts by weight, the prepared black atractylodes rhizome is 15 parts by weight, the turmeric is 10 parts by weight, the unprocessed germinated barley is 15 parts by weight, the villous amomum fruit is 6 parts by weight, the coix seed is 10 parts by weight, the kelp is 10 parts by weight, the peach seed is 10 parts by weight, the tall gastrodia tuber is 10 parts by weight, the fuling is 12 parts by weight, the dried tangerine peel is 10 parts by weight, the seaweed is 20 parts by weight, the bitter apricot seed is 10 parts by weight, the cardamon fruit is 3 parts by weight, the perilla fruit is 10 parts by weight, the oriental waterplantain rhizome is 10 parts by weight, the ricepaperplant pith is 6 parts by weight, the Chinese waxgourd peel is 20 parts by weight, the kudzu vine root is 20 parts by weight, the unprocessed hawthorn fruit is 20 parts by weight, the milkvetch root is 10 parts by weight, the rice beans is 10 parts by weight, the lotus leaf is 20 parts by weight, the fortune eupatorium herb leaf is 10 parts by weight, the unprocessed cattail pollen is 10 parts by weight, the unprocessed rhubarb root and rhizome is 2 parts by weight, the inner membrane of chicken gizzard is 6 parts by weight, the white mustard seed is 12 parts by weight, the agastache rugosa is 8 parts by weight, the radish seed is 12 parts by weight, the xylitol is 30 parts by weight, the donkey-hide gelatin is 20 parts by weight, and the tortoise-plastron gelatin is 20 parts by weight.

4. A processing method for the Chinese herbal oral paste for conditioning phlegm-dampness constitution of claim 1, comprising the following steps in sequence: preparation of materials, soaking, decoction, concentration, and collecting an oral paste.

5. The processing method for the Chinese herbal oral paste for conditioning phlegm-dampness constitution of claim 4, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

6. The processing method for the Chinese herbal oral paste for conditioning phlegm-dampness constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning phlegm-dampness constitution of claim 6, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning phlegm-dampness constitution of claim 7, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

9. The processing method for the Chinese herbal oral paste for conditioning phlegm-dampness constitution of claim 8, wherein the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

10. The processing method for the Chinese herbal oral paste for conditioning phlegm-dampness constitution of claim 9, wherein the melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

11. A processing method for the Chinese herbal oral paste for conditioning phlegm-dampness constitution of claim 2, comprising the following steps in sequence: preparation of materials, soaking, decoction, concentration, and collecting an oral paste.

12. The processing method for the Chinese herbal oral paste for conditioning phlegm-dampness constitution of claim 11, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

13. The processing method for the Chinese herbal oral paste for conditioning phlegm-dampness constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning phlegm-dampness constitution of claim 13, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning phlegm-dampness constitution of claim 14, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

16. The processing method for the Chinese herbal oral paste for conditioning phlegm-dampness constitution of claim 15, wherein the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

17. The processing method for the Chinese herbal oral paste for conditioning phlegm-dampness constitution of claim 16, wherein the melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

18. A processing method for the Chinese herbal oral paste for conditioning phlegm-dampness constitution of claim 3, comprising the following steps in sequence: preparation of materials, soaking, decoction, concentration, and collecting an oral paste.

19. The processing method for the Chinese herbal oral paste for conditioning phlegm-dampness constitution of claim 18, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

20. The processing method for the Chinese herbal oral paste for conditioning phlegm-dampness constitution of claim 19, wherein the soaking step is: soaking the cleaned raw materials with 8-10 folds of water for 8-15 h, with the water over the raw materials by 10-20 cm.

* * * * *